US010966637B2

(12) United States Patent
Glöckl

(10) Patent No.: US 10,966,637 B2
(45) Date of Patent: Apr. 6, 2021

(54) WORKPLACE ANALYSIS SYSTEM

(71) Applicant: aeris GmbH, Haar bei Munich (DE)

(72) Inventor: Josef Glöckl, Munich (DE)

(73) Assignee: AERIS GMBH, Haar bei Munchen (DE)

( * ) Notice: Subject to any disclaimer, the term of this patent is extended or adjusted under 35 U.S.C. 154(b) by 374 days.

(21) Appl. No.: 15/814,526

(22) Filed: Nov. 16, 2017

(65) Prior Publication Data

US 2018/0197126 A1 Jul. 12, 2018

(30) Foreign Application Priority Data

Jan. 8, 2017 (DE) ..................... 10 2017 100 884.5

(51) Int. Cl.

| | |
|---|---|
| ***A61B 5/11*** | (2006.01) |
| ***A61B 5/00*** | (2006.01) |
| *G06Q 10/06* | (2012.01) |
| *G06K 9/00* | (2006.01) |

(52) U.S. Cl.

CPC ............... *A61B 5/1116* (2013.01); *A61B 5/11* (2013.01); *A61B 5/6889* (2013.01); *A61B 5/6898* (2013.01); *G06K 9/00342* (2013.01); *G06K 9/00382* (2013.01); *G06Q 10/0633* (2013.01)

(58) Field of Classification Search

CPC .............. G08B 21/22; G08B 13/19645; G08B 13/019698; A61B 5/68; A61B 5/026; A61B 5/1116; A61B 5/1118; A61B 5/6887; A61B 5/6889; A61B 5/70; A61B 2503/20;

(Continued)

(56) References Cited

U.S. PATENT DOCUMENTS 7,339,471 B1 * 3/2008 Chan .................... G08B 15/002 315/159

2006/0012545 A1 1/2006 Kishi et al.

(Continued)

*Primary Examiner* — Van T Trieu

(74) *Attorney, Agent, or Firm* — Scully Scott Murphy and Presser

(57) ABSTRACT

The invention relates to a workplace analysis system (1) in a work area (10) for the acquisition and analysis of the presence of a person (P) to be monitored in several differently defined zones (A, B, C) of the work area (10) and of at least the temporal duration of stay ($t_A$, $t_B$, $t_C$) of the person (P) to be monitored within the zones (A, B, C), wherein in the workplace analysis system (1) at least one acquisition device (20) is provided, which is designed to detect and to acquire the presence and the duration of stay ($t_A$, $t_B$, $t_C$) of the person (P) to be monitored in the respective zones (A, B, C), and an analysis device (30) is provided, which is designed to analyze and evaluate the presence and the duration of stay ($t_A$, $t_B$, $t_C$) of the person (P) to be monitored in the respective zones (A, B, C).

12 Claims, 2 Drawing Sheets

(58) Field of Classification Search
CPC ......... A61B 2503/24; A61B 5/00; A61B 5/11; G06K 9/00771; G06K 9/00778
See application file for complete search history.

(56) References Cited

U.S. PATENT DOCUMENTS

| | | | | |
|---|---|---|---|---|
| 2008/0021731 | A1* | 1/2008 | Rodgers | A61B 5/1113 705/2 |
| 2012/0323090 | A1* | 12/2012 | Bechtel | A61M 21/02 600/306 |
| 2014/0313330 | A1* | 10/2014 | Carey | G06K 9/00778 348/143 |
| 2015/0010204 | A1* | 1/2015 | Iwai | G06K 9/00335 382/103 |
| 2015/0025327 | A1* | 1/2015 | Young | A61B 5/1115 600/301 |
| 2015/0199698 | A1* | 7/2015 | Yoshitake | G06K 9/00335 705/7.34 |
| 2016/0117627 | A1* | 4/2016 | Raj | G06Q 10/06398 705/7.42 |
| 2016/0192864 | A1 | 7/2016 | Booij et al. | |
| 2016/0275534 | A1* | 9/2016 | Iwai | G06Q 30/06 |
| 2017/0105095 | A1* | 4/2017 | Um | H04W 4/80 |
| 2017/0308843 | A1* | 10/2017 | Iwai | G08B 25/08 |
| 2017/0344834 | A1* | 11/2017 | Hirakawa | G06K 9/00771 |
| 2019/0050630 | A1* | 2/2019 | Baduge | G06K 9/00597 |

* cited by examiner

WORKPLACE ANALYSIS SYSTEM

FIELD OF THE INVENTION

The invention relates to a workplace analysis system for analyzing the movement and/or body position profile of a person in a work area divided into differently defined zones.

BACKGROUND OF THE INVENTION

The increasing work time spent at desks requires strengthened ergonomic measures for preventing tension, pain and long-term injury of the locomotor apparatus, particularly in persons with a large amount of deskwork.

In addition to the above-mentioned health improvements, such ergonomic measures also increase the efficiency, since, as a result of the measures, the ability to think and concentrate is also increased.

Various workplace analysis systems are already known in the prior art; however, they tend to acquire data one time only on the suitability for prevention of injuries and to identify optimization options for that purpose. However, such systems have the disadvantage that they do not motivate a person to make use of measures and possibilities beneficial to health. Furthermore, systems are known in the prior art, which, although they provide an indication for improvement, comprise no possibility for the acquisition of data on the actual activities or the actual position of the person.

SUMMARY OF THE INVENTION

Therefore, the aim of the invention is to overcome the above-mentioned disadvantages and to provide a workplace analysis system which acquires the movement spaces, the body position, and the durations of stay of a person in the movement spaces or in the body position, analyzes and extrapolates the acquired data, and compares the acquired data with predetermined values or values preset by the person. Furthermore, the aim of the workplace analysis system is to store and display the acquired data, and to inform the person when a preset value has been reached and to motivate the person to at least change the body position.

This aim is achieved by the combination of features according to claim 1.

DETAILED DESCRIPTION OF THE INVENTION

Figure 1:
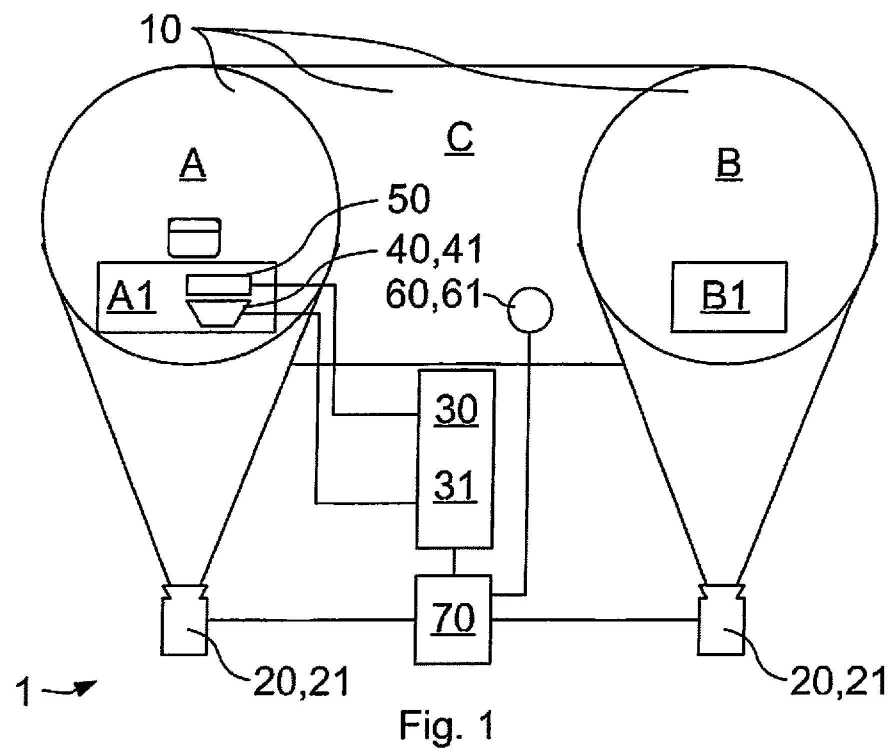
FIG. 1 shows a diagrammatic representation of a workplace analysis system.

Proposed according to the invention is a workplace analysis system in a work area for the acquisition and analysis of the presence and/or of characteristic values of a person to be monitored in several differently defined zones of the work area, and of at least the temporal duration of stay of the person to be monitored within the zones. In the workplace analysis system, at least one acquisition device is provided, which is designed to detect and acquire the presence and the duration of stay of the person to be monitored in the respective zones, and an analysis device is provided, which is designed to analyze and evaluate the presence and the duration of stay of the person to be monitored in the respective zones.

Furthermore, in an advantageous design variant, the acquisition device is designed to acquire the body position, the body temperature, the attentiveness and/or the ability to concentrate of the person to be monitored, wherein the analysis device is designed moreover to analyze, evaluate, compare with target values and/or display the body position, the body temperature, the attentiveness and/or the ability to concentrate of the person to be monitored.

The ability to concentrate is to be acquired, for example, by detecting the fatigue or exhaustion of the person to be monitored via the gestures, the inclination angle of the head and/or the intervals between blinking and the duration of blinking.

In an additional advantageous design form, it is advantageous that, in a first zone of the differently defined zones, a seated workplace is provided and/or wherein, in a second zone of the differently defined zones, a standing workplace is provided. Here, the seated workplace comprises a suitable work surface such as, for example, a desk or an assembly station, as well as a seat. The standing workplace comprises a suitable standing place, in addition to a standing work surface suited for this purpose, at which it is possible to work standing. The standing place can comprise, for example, a standing stool and/or an active floor surface, which make/makes it more comfortable to stand, while at the same time having an ergonomically advantageous effect on the body position of the person to be monitored.

Furthermore, it is advantageous that, in a design form, at least at the seated workplace, an active dynamic chair or rocking stool is provided, which advantageously influences the body position of the person to be monitored while the sitting.

In an additional advantageous design form, the at least one acquisition device acquires characteristic values comprising the body temperature and/or the heart rate and/or the heart rate variability and/or the pulse rate and/or the blood pressure and/or the blood sugar level and/or the flow rate of the blood and/or the oxygen saturation of the blood.

In an advantageous design variant, a third zone of the differently defined zones represents a movement space between and/or next to the zones, or comprises a movement space. The movement space or third zone adjoins the first and/or second zone(s) directly or can be arranged spaced apart therefrom. For example, the movement space or third zone can be present in the same space in which the first and/or second zone is/are located, but the third zone can also be arranged spaced apart from the space in a second space. Here the movement space is a surface on which the person to be monitored can move. For example, it should be possible to walk back and forth in the movement space, for which purpose it covers at least around 3 $m^2$. In the movement space, additional work stations can also be provided, at which, for example, work is to be performed for a short duration in a crouched or stretched position.

In a development, advantageously for the workplace analysis system, the acquisition device comprises at least one sensor.

Furthermore, it is advantageous that, in an additional design variant, in each case a sensor for the detection and acquisition of the person to be monitored or for the acquisition of characteristic values of the person to be monitored is provided at least in the first and in the second zone.

In an advantageous variant, the detection and acquisition of the person to be monitored in the third zone is provided in each case by one sensor of the first and/or second zone. For example, the person to be monitored in the third zone can be defined or acquired via the absence of the person to be monitored in the first and/or second zone. Furthermore, the acquisition region of the sensor in the first and/or second zone can be divided into a near region and a far region, wherein it can be defined that the near region defines and monitors the first and/or second zone, and the far region defines and/or monitors another zone, for example, the third zone. By dividing the acquisition region of a sensor into a near region and a far region, two zones of the differently defined zones or the person to be monitored in two zones can be monitored and acquired by a sensor and concretely distinguished.

In a design variant, the sensor advantageously is an ultrasound echo sensor or an infrared array sensor.

Furthermore, in an advantageous design variant, the acquisition device comprises a sensor device that can be worn by the person. The sensor device can be implemented, for example, in the form of a capsule, a dongle, a wrist band or a wrist watch and it acquires, for example, the steps taken by the person to be monitored, the heart rate, the number of stair steps climbed and/or sports activities and it continuously or at intervals, by wireless or wire connection, transmits this data to the analysis device in order to be analyzed there. Here it is possible to distinguish which data were recorded in which zone, so that the data can be assigned uniquely to the zones. The wireless transmission can be implemented, in particular, via the Bluetooth Low Energy radio technology. The sensor device moreover can be arranged on or under the skin of the person to be monitored. By means of the sensor device which can be worn by the person to be monitored, the person to be monitored can moreover be distinguished for the acquisition system from other persons, so that the acquisition or monitoring of persons not to be monitored can be prevented.

Furthermore, in a development form, it is advantageous that the acquisition device comprises a means for transmitting the acquired data electronically via a data interface to the analysis device. The means, for example, is an electrically conductive connection between the acquisition device and the analysis device, wherein the data interface can be configured as an adapter between sensor and the analysis device or directly by the analysis device. If necessary, the data interface is used here to convert the data as generated by the acquisition device into a form in which it can be interpreted by the analysis device. The data interface can also be designed as a distributor or a collection site, so that several sensors transfer the respective data acquired by them via the data interface to the analysis device.

In an additional advantageous design form, the analysis device is designed to store data acquired by the acquisition device, classify the acquired data depending on the zone in which it was acquired, process, evaluate and/or extrapolate the acquired data, and, in particular, compare the acquired data with stored target values. When values represented by the data reach or approach preset values, the values or data are displayed, stored or transmitted electronically to a data collection site.

Depending on the zones, an advantageous development form provides for performing a classification indicating whether the person to be monitored is sitting, standing, absent or moving. Depending on the zones, the body position of the person to be monitored can be classified. If the person to be monitored is in the first zone, this is classified, for example, as sitting, in the second zone, for example, as standing, and in the third zone, for example, as moving.

In a design variant, it is advantageous that the workplace analysis system comprises a display device designed to display the data stored, classified, processed, evaluated and/or extrapolated by the analysis device, wherein the analysis device is preferably a stand-alone computer, and the display device is preferably a screen connected to the stand-alone computer.

In an additional development form, it is advantageous moreover that an input device is provided, for manually entering or modifying person-related data and/or a person-specific target stay pattern of the person for the respective zones, which can be compared by means of the analysis device with the actually acquired data. For example, it is possible to preset how many hours per workday should be spent standing, lying or in other body positions. Moreover, for example, the age, name, physical or health characteristics and a picture of the person to be monitored can be entered or stored, whereby, for example, the data, the operation of the analysis device, recommendations for presetable values, the display of the data, and much more can be personalized. As a result of the classification depending on the zones, the target stay pattern corresponds to a target body position pattern. From both the target stay pattern and the target body position pattern, comparison data and preset values are obtained, which are processed and treated by the analysis device.

Advantageously, a design form comprises a warning device which is designed to display or symbolize at least one value of the data acquired by the acquisition unit.

Here, furthermore, a development form is advantageous, in which the warning device displays the duration of stay of the person to be monitored in the respective zone and, in particular, displays reaching of and/or a deviation from the target stay pattern stored in the system.

In a special, advantageous design variant, the warning device is a light or lamp which shines more brightly with increasing value of the duration of stay in the respective zone, and which, when a preset limit value stored in the target stay pattern has been reached, blinks until the person to be monitored moves from the current zone into another zone or changes the body position.

The acquisition device is designed in an advantageous design variant in such a manner that it is not worn on the body, but remains stationary.

Furthermore, in another preferred embodiment the display device, the input device and/or the analysis device is/are a wearable mobile device.

In a development form, the person to be monitored can be distinguished advantageously from other persons by suitable measures. Suitable measures are, for example, movement tracking by the acquisition device or the individualization and recognition of the person to be monitored by video systems or transceiver devices such as an RFID transceiver system.

The above disclosed features can be combined in any manner to the extent technically possible and not in contradiction with one another.

Furthermore, in an advantageous development, means are provided in order to motivate the monitored person depending on the detected stay pattern and/or body position pattern to leave the zone in which he/she is located. Such means can comprise, for example, current interruption in a zone by a circuit breaker, visual or acoustic indications or messages in a zone, or the like.

Other advantageous developments of the invention are characterized in the dependent claims and represented in greater detail below together with the description of the preferred design of the invention in reference to the figures.

The figures are diagrammatic examples. Identical reference numerals in the figures denote functionally and/or structurally identical features.

In FIG. 1, a workplace analysis system 1 is represented, wherein the work area 10 is subdivided into a first zone A, a second zone B and a third zone C. In the first zone A, a seated workplace A1 is arranged, and, in the second zone B spaced apart from the first zone A, a standing workplace B1 is arranged. Between the first and the second zone A, B, the third zone C is provided, which forms a movement space, in which a person to be monitored, who is not shown, can move. In the first zone A, in the area of the seated workplace A1, which is determined by a desk as work surface and an active dynamic chair, the input device 50 designed as a keyboard and the display device 40 designed as the screen 41 are arranged. Both the input device 50 and the display device 40 are electronically connected to the analysis device 30 which is designed as stand-alone computer 31. A sensor 21 and an additional sensor 21, which form the acquisition device 20, are designed as ultrasound echo sensors. The sensor 21 here monitors the presence of the person to be monitored in the first zone A, and the additional sensor 21 monitors the presence of the person to be monitored in the second zone B. The presence of the person to be monitored in the third zone C is here defined by the absence of the person to be monitored in the first zone and in the second zone A, B.

The sensors 21 are electrically connected to a data interface 70. The data generated by the sensors is transmitted in each case via an electrical connection line between a sensor 21 and the data interface 70 to the data interface 70. The data are converted in the data interface 70 and transmitted collected via an electrical connection to the analysis device 30. In the analysis device 30 designed as stand-alone computer 31, the data transmitted by the data interface 70 are compared with stored data and extrapolated. The results or a graphic representation of the data and the evaluation results are displayed via the screen 41.

A value which represents the current duration of stay of the person to be monitored in the current zone in which the person to be monitored is located, when a first preset limit value has been reached, is converted by the analysis device 30 and transmitted via the data interface 70 to the warning device 60. The warning device 60, which is designed as lamp 61 arranged in the third zone C, becomes brighter stepwise due to the value transmitted to it, starting at the first preset limit value and until a second preset limit value has been reached. When the second preset limit value has been reached, which corresponds to the target specification for the maximum duration of stay at one time in the current zone, the warning device 60 or the lamp 61 starts to blink symbolizing that the person to be monitored should leave the current zone as soon as possible and continue his/her activity in another zone.

Figure 2:
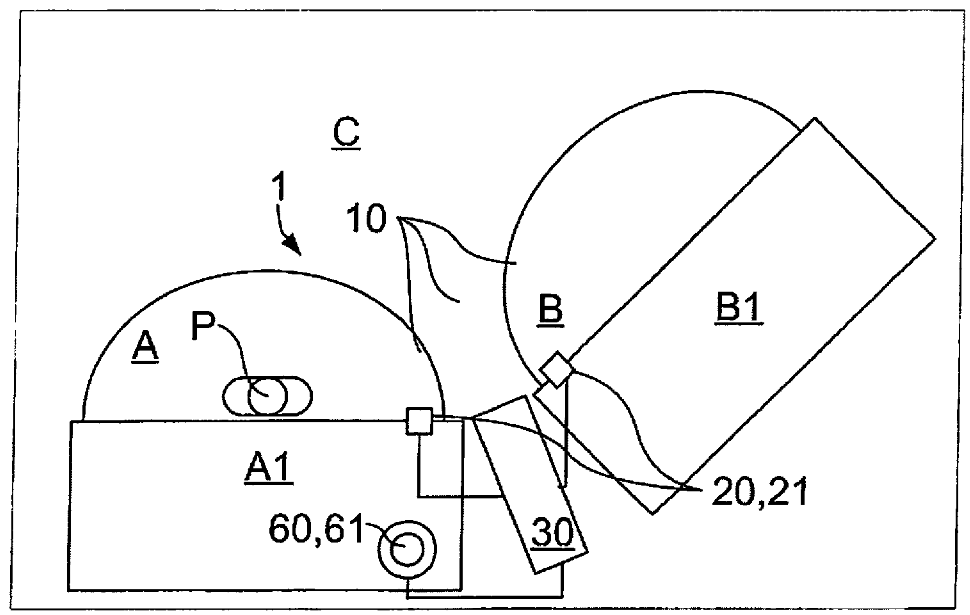
FIG. 2 shows another diagrammatic representation of a workplace analysis system.

In FIG. 2, a workplace analysis system 1 is represented, which is similar to the workplace analysis system 1 shown in FIG. 1. However, the data interface is integrated directly in the analysis device 30, so that the components of the acquisition device 20 and the warning device 60 are connected electronically directly to the analysis device 30. Furthermore, the third zone C is not provided between the first and the second zone A, B, but rather encloses said zone.

Figure 3:
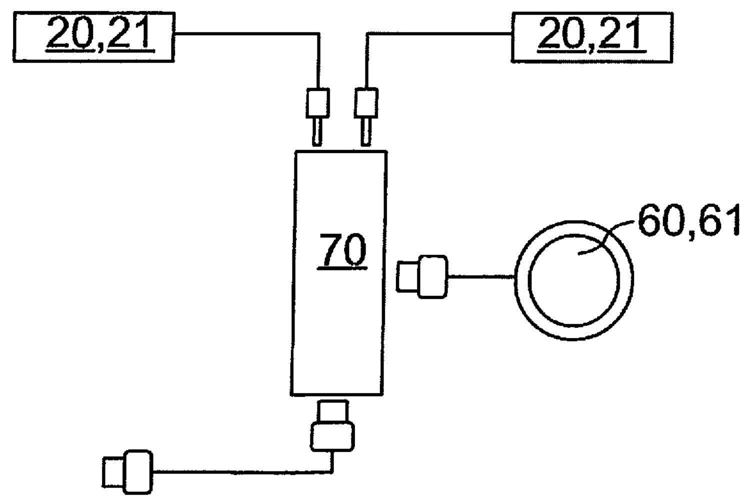
FIG. 3 shows a diagrammatic representation of sensors, of a warning device and of a data interface.

FIG. 3 shows the components of the workplace analysis system 1, which usually are not yet present at a normal workplace. The acquisition device 20 designed as sensor 21 can be connected in each case via a cable running from the sensors 21 to the data interface 70. The data interface 70 has a plurality of plug sockets, whereby the cables of the sensors 21 and the plug contacts of the cables can be connected to the data interface 70. The warning device 60, which is designed as lamp 61, can be connected via a USB connection cable running from it to the data interface 70. The data interface 70 can be connected via a USB cable to the analysis device 30.

Figure 4:
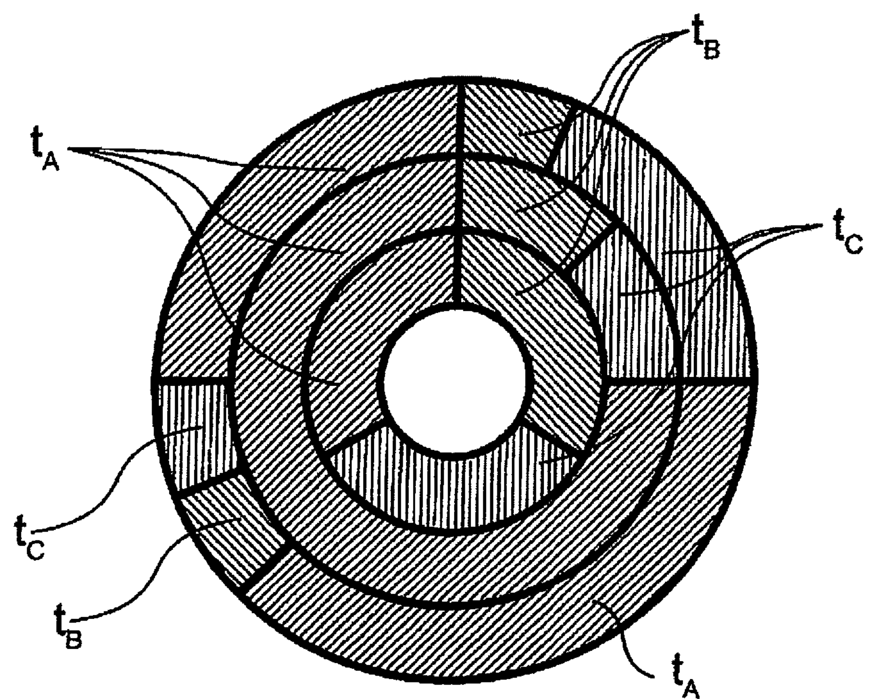
FIG. 4 shows a daily profile of the body position or of the durations of stay of a person to be monitored in the zones.

FIG. 4 shows the distribution of the proportions of $t_A$, $t_B$ and $t_C$ in an 8-hour work day. The innermost ring here represents the target values collected, that is to say the proportion of the 8 hours that should be spent per work day sitting $t_A$, standing $t_B$, and moving $t_C$. The middle ring represents the durations $t_A$, $t_B$ and $t_C$ which have actually been spent sitting, standing or moving by the person to be monitored. The outermost ring also represents the actual durations $t_A$, $t_B$ and $t_C$ wherein these durations have not been totaled, but rather in each case represent the durations spent at one time in the respective body position or position or zone.

The invention, in the design thereof, is not limited to the above-indicated preferred embodiment examples. Instead, a number of variants are conceivable, which use the represented solution, even in designs of fundamentally different type. For example, several zones could be monitored simultaneously by an individual sensor, or zones could be monitored simultaneously by several sensors.

The invention claimed is:

1. A workplace analysis system in a work area for the acquisition and analysis of the presence and/or of characteristic values of a person (P) to be monitored in several differently defined zones (A, B, C) of the work area and of at least a temporal duration of stay ($t_A$, $t_B$, $t_C$) of the person (P) to be monitored within the zones (A, B, C), wherein, in the workplace analysis system, at least one acquisition device is provided, which is designed to detect and to acquire the presence and duration of stay ($t_A$, $t_B$, $t_C$) of the person (P) to be monitored in the zones (A, B, C), and an analysis device is provided, which is designed to analyze and evaluate the presence and the duration of stay ($t_A$, $t_B$, $t_C$) of the person (P) to be monitored in the zones (A, B, C), wherein the acquisition device comprises at least one sensor, and wherein, in each case, the at least one sensor is provided for the detection and acquisition of the person (P) to be monitored or for the acquisition of characteristic values of the person (P) to be monitored at least in zone (A) and/or zone (B), and wherein, in each case, the detection and acquisition of the person (P) to be monitored in zone (C) is provided, in each case, by the at least one sensor of zone (A) and/or zone (B), and wherein the sensor is an ultrasound echo sensor or an infrared array sensor, and wherein the analysis device is designed to store data acquired by the acquisition unit, to classify the acquired data depending on the zones (A, B, C) in which it was acquired, to process, evaluate and/or extrapolate the acquired data and, to compare the acquired data with stored target values, and wherein the analysis device is designed to classify, depending on the zones (A, B, C), whether the person (P) to be monitored is sitting, standing, absent or moving.

2. The workplace analysis system according to claim 1, wherein a seated workplace (A1) is provided in zone (A) and/or wherein a standing workplace (B1) is provided in zone (B).

3. The workplace analysis system according to claim 2, wherein an active dynamic chair or rocking stool is provided in the seated workplace (A1).

4. The workplace analysis system according to claim 1, wherein the at least one acquisition device acquires characteristic values comprising body temperature and/or heart rate and/or heart rate variability and/or pulse rate and/or blood pressure and/or blood sugar level and/or blood flow rate and/or oxygen saturation of the blood.

5. The workplace analysis system according to claim 1, wherein zone (C) represents or comprises a movement space between or next to the zones (A, B).

6. The workplace analysis system according to claim 1, wherein the acquisition device comprises a sensor device which can be worn by person (P).

7. The workplace analysis system according to claim 1, wherein, the acquisition device comprises a means for transmitting acquired data electronically via data interface to the analysis device.

8. The workplace analysis system according to claim 1 further comprising a display device which is designed to display the data stored, classified, processed, evaluated and/or extrapolated by the analysis device, wherein the analysis device is preferably a stand-alone computer, and the display device is preferably a screen connected to the stand-alone computer.

9. The workplace analysis system according to claim 1 further comprising an input device is moreover provided, in order to manually input or modify person-related data and/or a person-specific target stay pattern of the person (P) for the respective zones (A, B, C), which can be compared with the actually acquired data by means of the analysis device.

10. The workplace analysis system according to claim 1 further comprising a warning device which is designed to display at least one value of the data acquired by the acquisition device.

11. The workplace analysis system according to claim 10, wherein the warning device displays the presence and duration of stay ($t_A$, $t_B$, $t_C$) of the person (P) to be monitored in the respective zone (A, B, C) and, in particular, reaching of and/or a deviation from a stored target stay pattern.

12. The workplace analysis system according to claim 11, wherein the warning device is a light which shines more brightly with increasing value of the presence and duration of stay in the respective zone (A, B, C), and which, when a preset limit value stored in the target stay pattern has been reached, blinks until the person (P) to be monitored moves from a current zone into another zone.

* * * * *

UNITED STATES PATENT AND TRADEMARK OFFICE

CERTIFICATE OF CORRECTION

PATENT NO. : 10,966,637 B2
APPLICATION NO. : 15/814526
DATED : April 6, 2021
INVENTOR(S) : Joseph Glöckl It is certified that error appears in the above-identified patent and that said Letters Patent is hereby corrected as shown below:

On the Title Page

(72) Inventor should read:
Joseph Glöckl, Kirchheim (DE)

(30) Foreign Application Priority Data should read:
Jan. 18, 2017 (DE)........................10 2017 100 884.5

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*